United States Patent
Chi et al.

(10) Patent No.: US 10,730,822 B1
(45) Date of Patent: Aug. 4, 2020

(54) PROCESS FOR MAKING ALICYCLIC POLYCARBOXYLIC ACIDS OR THEIR DERIVATIVES

(71) Applicant: CPC Corporation, Taiwan, Kaohsiung (TW)

(72) Inventors: Ching-Fa Chi, Chiayi (TW); Ying-Chien Yang, Chiayi (TW); Yi-Hui Chen, Chiayi (TW); Yih-Ping Wang, Chiayi (TW); Chyi-Liuh Ho, Chiayi (TW)

(73) Assignee: CPC CORPORATION, TAIWAN, Kaohsiung (TW)

(*) Notice: Subject to any disclaimer, the term of this patent is extended or adjusted under 35 U.S.C. 154(b) by 0 days.

(21) Appl. No.: 16/353,920

(22) Filed: Mar. 14, 2019

(30) Foreign Application Priority Data

Feb. 15, 2019 (TW) ............................. 108105051 A

(51) Int. Cl.
| | |
|---|---|
| *C07C 67/303* | (2006.01) |
| *B01J 27/13* | (2006.01) |
| *B01J 21/04* | (2006.01) |
| *B01J 21/10* | (2006.01) |

(52) U.S. Cl.
CPC ............. *C07C 67/303* (2013.01); *B01J 21/04* (2013.01); *B01J 21/10* (2013.01); *B01J 27/13* (2013.01)

(58) Field of Classification Search
CPC ......... C07C 67/303; B01J 21/10; B01J 27/13; B01J 21/04
See application file for complete search history.

(56) References Cited

U.S. PATENT DOCUMENTS

| | | | |
|---|---|---|---|
| 6,284,917 B1 | 9/2001 | Brunner et al. | |
| 7,595,420 B2 | 9/2009 | Schlosberg et al. | |
| 8,586,784 B2 | 11/2013 | Grass et al. | |
| 8,722,922 B2 * | 5/2014 | Chang | ............... B01J 37/0201 560/127 |

FOREIGN PATENT DOCUMENTS

| | | |
|---|---|---|
| CN | 10265818 B | 4/2014 |
| TW | I273101 B | 2/2007 |
| TW | I414513 B | 11/2013 |

* cited by examiner

*Primary Examiner* — Jafar F Parsa
*Assistant Examiner* — Blaine G Doletski
(74) *Attorney, Agent, or Firm* — Chun-Ming Shih

(57) ABSTRACT

The present invention discloses a process for making alicyclic polycarboxylic acids or their derivatives, referring to a process for hydrogenating aromatic polycarboxylic acids or their derivatives in the presence of hydrogen and a catalyst to form alicyclic polycarboxylic acids or their derivatives, and the catalyst comprises at least one active metal of group VIIIB transition elements of the periodic table of elements, and a catalyst support comprising group IIA and group IIIA elements in a specific weight ratio.

13 Claims, 1 Drawing Sheet

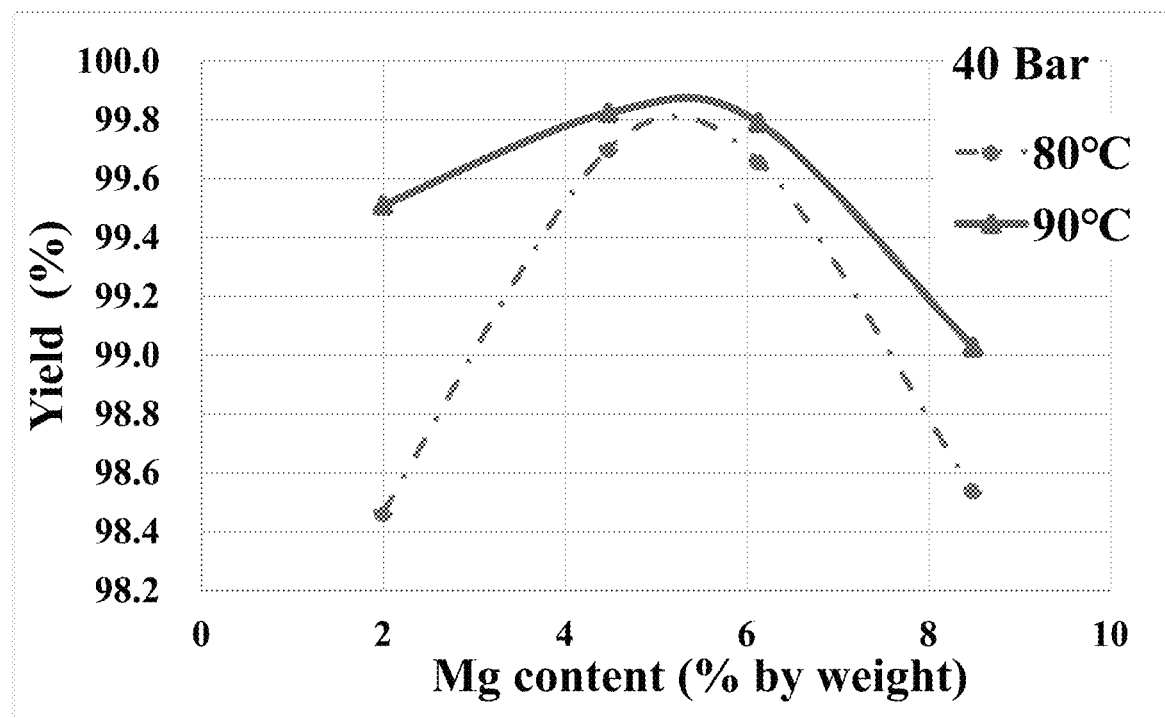

PROCESS FOR MAKING ALICYCLIC POLYCARBOXYLIC ACIDS OR THEIR DERIVATIVES

BACKGROUND OF THE INVENTION

Field of the Invention

The present invention relates to hydrogenation of aromatic compounds, and particularly a hydrogenation process for forming corresponding alicyclic polycarboxylic acids or their derivatives from aromatic polycarboxylic acids or their derivatives by hydrogenation reaction.

Description of the Prior Art

Hydrogenation reaction is a reaction in which a carbon-carbon double bond is reduced to a saturated alkane product with hydrogen in the presence of a catalyst, which is commonly found in processes for oil refining, food, pharmaceutical, and general chemical processing. For example, hydrogenation reduces the proportion of unsaturated fat in vegetable oils; hydrogenation of copolymer having unsaturated chains segments to change the molecular structure and properties, or aromatic epoxy resin through hydrogenation of benzene ring can improve deterioration phenomenon caused by UV light irradiation. Hydrogenated alicyclic polycarboxylic acids can be used in functional polyimide and curing agents for functional epoxy resins, etc. Also, hydrogenated cyclohexane dicarboxylate can be used as a plasticizer for substituting phthalate, used in the processing of polyvinyl chloride (PVC), or as a coating material, a filling and reinforcing material, a processing agent, and the like. For PVC processing Currently, phthalate series products, including derivatives such as dibutyl phthalate (DBP), dioctyl phthalate (DOP) or diisononyl phthalate (DINP) are the most widely used plasticizers in the PVC processing. However, in recent years, such substances have been claimed to be harmful to human health, and they are gradually prohibited from being used in some applications such as baby products. Therefore, some aliphatic dicarboxylic acid esters are regarded as environmentally friendly substances to replace phthalates as plasticizers, for example, 1,2-Cyclohexane dicarboxylic acid diisononyl ester, this compound is produced by saturating the benzene rings through hydrogenation reaction of benzenepolycarboxylic acid derivatives to remove its toxicity.

The catalyst used in hydrogenation reaction is a crucial point. In the prior art, the U.S. Pat. No. 6,284,917 B1, for example, discloses that bimodal alumina containing macropores can be used as a support for making a supported ruthenium catalyst to produce the corresponding alicyclic carboxylic acid esters using a high pressure batchwise stirred reactor (autoclave) at 80° C. and a pressure range of 100 to 200 bar.

The Chinese patent CN102658182B discloses using phosphorus-modified alumina (P—$Al_2O_3$) as a support, which can be made into a catalyst after being loaded with nickel element, and using a continuous fixed bed reactor at 150-200° C. and a pressure range of 30-150 bar to produce the corresponding alicyclic carboxylic acid esters.

The U.S. Pat. No. 7,595,420 B2 discloses that an ordered mesoporous silica, MCM 41, can be used as a catalyst support for making a supported ruthenium catalyst to produce the corresponding alicyclic carboxylic acid esters using a high pressure batchwise stirred reactor (autoclave) at 120° C. and a pressure range of 58 to 200 bar.

The U.S. Pat. No. 8,722,922 B2 discloses a supported catalyst, supported group VIIIB such as palladium and ruthenium on a support containing 2A alkali metal alumina (2A—$Al_2O_3$), can be used to produce the corresponding alicyclic carboxylic acid esters using a fixed bed reactor at 100-250° C. and a pressure range of 1-50 bar.

The U.S. Pat. No. 8,586,784 B2 discloses that a supported catalyst can be made by using titanium dioxide ($TiO_2$) as a support, and the supported catalyst can be used to produce the corresponding alicyclic carboxylic acid esters using a continuous fixed bed reactor at 100° C. and a pressure range of 100 bar.

The Taiwanese patent I414513B discloses a reaction tank with a gas-guiding and stirring device containing capability of pumping and exhausting, and in the presence of palladium catalyst and hydrogen, hydrogenation reaction is carried out at 180° C. to 200° C. and a pressure range of 19.6 to 39.2 bar to produce the corresponding alicyclic carboxylic acid esters. Although the yield can reach 99.9-99.995%, the catalyst needs to be filtered to separate from the hydrogenated products and recovered.

The Taiwanese patent I273101 discloses using titanium dioxide distributed with small pores and medium pores as a catalyst support, and loading ruthenium metal on it to give a catalyst which can be used for hydrogenating aromatic compounds into alicyclic compounds at 3 to 300 bar and 50 to 250° C.

It is known from the above-mentioned prior art that the hydrogenation of aromatic polycarboxylic acid esters need to be carried out in an environment of high pressure (>100 bar) or with temperature higher than 100° C. or with high pressure and high temperature in most inventions, so that the hydrogenation rate of benzene rings can reach higher than 90%, which makes the investment cost high, and the subsequent operation and maintenance costs are high.

SUMMARY OF THE INVENTION

The present invention provides a process for making alicyclic polycarboxylic acids or their derivatives, and particularly a hydrogenation process for forming corresponding alicyclic polycarboxylic acids or their derivatives from aromatic polycarboxylic acids or their derivatives by hydrogenation reaction, the hydrogenation reaction can be carried out in a low pressure (<50 bar) and low temperature (<100° C.) environment, meanwhile, both the conversion and yield can reach above 99%.

The aromatic polycarboxylic acids provided by the present invention broadly refer to compounds formed with carboxylic acids, dicarboxylic acids, polycarboxylic acids, hydroxycarboxylic acids or the like contained in an aromatic structure. The aromatic chain segment can include benzenes, biphenyls, anthracenes, naphthalenes, polycyclic aromatic hydrocarbons, etc., such as benzene polycarboxylic acids, biphenyl polycarboxylic acids, naphthalene polycarboxylic acids, etc., and thus hydrogenation reaction of the benzene rings portion of different aromatic polycarboxylic acids or derivatives thereof can be carried out to produce saturated corresponding alicyclic polycarboxylic acids or derivatives thereof, particularly hydrogenation reaction of the benzene rings portion of the aromatic polycarboxylic acids or derivatives thereof to produce cyclohexane polycarboxylic acids or derivatives thereof. Aromatic polycarboxylic acids include phthalic acid, isophthalic acid, terephthalic acid, trimellitic acid, trimesic acid, hemimellitic acid, pyromellitic acid, and combinations of any two or more of the above. The aromatic polycarboxylic acid derivatives refer to monoesters, diesters and polyesters of aromatic polycarboxylic acids, and the esters include C1-C30 alkyl ester, C3-C30 cycloalkyl ester, and C1-C30 alkoxyalkyl ester. Preferably C2-$C_{20}$ alkyl ester, C3-C20 cycloalkyl ester, and C2-$C_{20}$ alkoxyalkyl ester. More preferably C3-$C_{18}$ alkyl ester, C4-$C_{18}$ cycloalkyl ester, and C3-$C_{18}$ alkoxyalkyl ester, wherein the carbon chain can be linear or branched. For example, dimethyl phthalate (DMP), dimethyl terephthalate (DMT), dimethyl isophthalate (DEP), dibutyl phthalate (DBP), diisooctyl phthalate (DOP), diisononyl phthalate (DINP), benzyl butyl phthalate (BBP), diisodecyl phthalate (DIDP), dioctyl terephthalate (DOTP), and combinations of any two or more of the above.

The present invention provides a hydrogenation process for forming corresponding alicyclic polycarboxylic acids or their derivatives from aromatic polycarboxylic acids or their derivatives by hydrogenation reaction, which can produce the corresponding alicyclic polycarboxylic acids and their derivatives at a low temperature and a low pressure. The process is performed under conditions of a catalyst, the catalyst comprises a catalyst support and active metals, wherein the catalyst support is composed of elements of groups IIA and IIIA of the periodic table of elements, and the active metals include group VIII B transition metal elements of the periodic table of elements. Compared with the conventional methods, generally, hydrogenation reaction needs to be carried out in a high-pressure hydrogen environment and at a suitable temperature, so that the catalyst can exhibit its catalytic activity. However, although increasing the reaction temperature can increase the reaction rate and increase the conversion, it is easy to cause a side reaction and bring about a decrease in the purity of the products. Further, because the hydrogenated products, alicyclic polycarboxylic acids or their derivatives, and the original reactants-aromatic, polycarboxylic acids or their derivatives, are similar in structure, they cannot be easily separated. In addition, the construction costs of high-pressure equipment, subsequent operation and maintenance are also potential costs, and the risk in industrial safety is easily increased. In order to solve the above problems, the present invention takes into consideration in enhancing the activity of the catalyst without compromising the purity of the products, and is achieved by using a catalyst. Therefore, it can be understood that the process of the present invention has substantial advantages compared with the prior art. The advantages are that the reaction temperature of the present invention only needs to be between 50 and 100° C., and the pressure between 1 and 40 bar, the conversion can be optimized to reach higher than 99.9%, and the product yield higher than 99.8%, which can reduce the cost of subsequent separation and improve the overall economic benefit.

The present invention is carried out for reaction under the conditions of a catalyst, the catalyst comprises a catalyst support and active metals, wherein the catalyst support comprises group IIA and group IIIA elements of the periodic table of elements; group IIA comprises magnesium (Mg), calcium (Ca), strontium (Sr), barium (Ba) or combinations of the above elements, and group IIIA comprises boron (B), aluminum (Al), gallium (Ga), indium (In) or combinations of the above elements; the active metals include group VIII B transition metal elements of the periodic table of elements, including nickel (Ni), platinum (Pt), palladium (Pd), ruthenium (Ru), rhodium (Rh) or combinations of the above elements. Wherein the active metals of group VIIIB account for 0.1-10% by weight of the total catalyst, wherein the preferred active metal is ruthenium (Ru). The preferred active metal of group IIA is magnesium (Mg), which accounts for 1-15% by weight of the entire catalyst support, the preferred ratio is 2.5-8 weight percentages, and the optimum ratio is 4 to 6.5 weight percentages; the preferred active metal of group IIIA is aluminum (Al).

The reaction process provided by the present invention can be carried out in the presence of solvents or other diluents, and compatibility with the main reactants should be taken into consideration when choosing the solvents or diluents in order to avoid phase separation or immiscibility, and the solvents or diluents should not participate in the reaction under hydrogenation conditions. The hydrogenation products themselves can also be used as solvents or diluents. The solvents used in the present invention comprise isopropanol, n-butanol, isobutanol, 2-ethyl hexanol, Isononyl alcohol, tetrahydrofuran, n-hexanol, etc.

The reactor used in the present process can be a continuous reactor (for example, trickle bed reactor, stir tank, multi-tube reactor, etc.) or a discontinuous reactor (such as batch reactor).

BRIEF DESCRIPTION OF THE DRAWINGS

The techniques of the present invention would be more understandable from the detailed description given herein below and the accompanying figures are provided for better illustration, and thus description and figures are not limitative for the present invention, and wherein:

The FIGURE is a graph showing the effect of changes in magnesium content (% by weight) in a catalyst support on the yield according to the present invention.

DETAILED DESCRIPTION OF THE PREFERRED EMBODIMENTS

Preparation Example

Dissolve 225.06 g of aluminum nitrate hexahydrate and a different number of grams of magnesium nitrate hexahydrate in 3000 mL of deionized water (the weight of magnesium nitrate hexahydrate is based on the weight of aluminum nitrate hexahydrate, the ratio of the magnesium content in the magnesia/alumina composite support is adjusted to 1 to 10% by weight), and then co-precipitated by adding a deionized water solution containing precipitation agent, such as one of ammonia water, sodium carbonate or sodium hydroxide or combination of both, adjusting the pH to 9-11, stirring well at 50-80° C. for 1-8 hours, a filter cake obtained by washing with water and filtering is dried at 110° C. and then calcined at a high temperature of 800° C. to obtain a magnesia/alumina composite catalyst support.

10 g of uniform support granules with 20-30 mesh size are acquired by pulverization and sieving, and an appropriate aqueous solution of ruthenium chloride ($RuCl_3$) is impregnated onto the catalyst support by incipient wetness impregnation method, and then calcined at a high temperature of 400° C. to obtain a catalyst with a ruthenium content of 5 weight percentages.

The present invention provides a hydrogenation reaction of aromatic polycarboxylic acids and derivatives thereof by using a catalyst comprising a catalyst support and active metals. The hydrogenation reaction is carried out using Di(2-ethylhexyl) phthalate (DEHP) as a reactant, and the reaction conditions and reaction results are as follows.

Embodiment 1

8 mL of the catalyst (the catalyst support is alumina) is filled in a reaction tube, and is reduced at 250° C. in a hydrogen atmosphere. After cooling, di(2-ethylhexyl) phthalate (DEHP) is sent into a tubular reactor by a charging pump for hydrogenation reaction, and the product is collected for quantitative measurement. The conversion and selectivity are analyzed by liquid chromatograph equipped with a tandem ultraviolet light spectrum detector (LC-UV) and gas chromatograph (GC), respectively. The operating conditions and corresponding experimental results are shown in Table 1:

TABLE 1

| Reactant | Reaction pressure (Bar) | Reaction temperature (° C.) | Reactant flow rate (ml/min) | Hydrogen flow rate (L/hr) | Conversion (%) | Yield (%) |
|---|---|---|---|---|---|---|
| DEHP | 40 | 80 | 0.053 | 6.87 | 95.80 | 82.87 |
| | 40 | 90 | 0.053 | 6.87 | 99.23 | 95.16 |

Embodiment 2

5.9 mL of the catalyst (the catalyst support is a magnesia/alumina composite support, and the content of magnesium in the catalyst support is 2 weight percentages) is filled in a reaction tube, and is reduced at 250° C. in a hydrogen atmosphere. After cooling, di(2-ethylhexyl) phthalate (DEHP) is sent into a tubular reactor by a charging pump for hydrogenation reaction, and the product is collected for quantitative measurement. The conversion and selectivity are analyzed by liquid chromatograph equipped with a tandem ultraviolet light spectrum detector (LC-UV) and gas chromatograph (GC), respectively. The operating conditions and corresponding experimental results are shown in Table 2:

TABLE 2

| Reactant | Reaction pressure (Bar) | Reaction temperature (° C.) | Reactant flow rate (ml/min) | Hydrogen flow rate (L/hr) | Conversion (%) | Selectivity (%) | Yield (%) |
|---|---|---|---|---|---|---|---|
| DEHP | 40 | 80 | 0.053 | 6.88 | 98.64 | 99.82 | 98.46 |
| | 40 | 90 | 0.053 | 6.88 | 99.79 | 99.72 | 99.51 |

Embodiment 3

6.3 mL of the catalyst (the catalyst support is a magnesia/alumina composite support, and the content of magnesium in the catalyst support is 4.5 weight percentages) is filled in a reaction tube, and is reduced at 250° C. in a hydrogen atmosphere. After cooling, di(2-ethylhexyl) phthalate (DEHP) is sent into a tubular reactor by a charging pump for hydrogenation reaction, and the product is collected for quantitative measurement. The conversion and selection rate are analyzed by liquid chromatograph equipped with a tandem ultraviolet light spectrum detector (LC-UV) and gas chromatograph (GC), respectively. The operating conditions and corresponding experimental results are shown in Table 3:

TABLE 3

| Reactant | Reaction pressure (Bar) | Reaction temperature (° C.) | Reactant flow rate (ml/min) | Hydrogen flow rate (L/hr) | Conversion (%) | Selectivity (%) | Yield (%) |
|---|---|---|---|---|---|---|---|
| DEHP | 40 | 80 | 0.056 | 7.18 | 99.83 | 99.87 | 99.70 |
| | 40 | 90 | 0.056 | 7.18 | 99.95 | 99.88 | 99.82 |

Embodiment 4

6.2 mL of the catalyst (the catalyst support is a magnesia/alumina composite support, and the content of magnesium in the catalyst support is 6.1 weight percentages) is filled in a reaction tube, and is reduced at 250° C. in a hydrogen atmosphere. After cooling, di(2-ethylhexyl) phthalate (DEHP) is sent into a tnbular reactor by a charging pump for hydrogenation reaction, and the product is collected for quantitative measurement. The conversion and selectivity are analyzed by liquid chromatograph equipped with a tandem ultraviolet light spectrum detector (LC-UV) and gas chromatograph (GC), respectively. The operating conditions and corresponding experimental results are shown in Table 4:

TABLE 4

| Reactant | Reaction pressure (Bar) | Reaction temperature (° C.) | Reactant flow rate (ml/min) | Hydrogen flow rate (L/hr) | Conversion (%) | Selectivity (%) | Yield (%) |
|---|---|---|---|---|---|---|---|
| DEHP | 40 | 80 | 0.054 | 6.94 | 99.81 | 99.85 | 99.66 |
| | 40 | 90 | 0.054 | 6.94 | 99.93 | 99.86 | 99.79 |

Embodiment 5

6.3 mL of the catalyst (the catalyst support is a magnesia/alumina composite support, and the content of magnesium in the catalyst support is 8.5 weight percentages) is filled in a reaction tube, and is reduced at 250° C. in a hydrogen atmosphere. After cooling, di(2-ethylhexyl) phthalate (DEHP) is sent into a tubular reactor by a charging pump for hydrogenation reaction, and the product is collected for quantitative measurement, The conversion and selectivity are analyzed by liquid chromatograph tandem ultraviolet light spectrum detector (LC-UV) and gas chromatograph (GC), respectively. The operating conditions and corresponding experimental results are shown in Table 5:

TABLE 5

| Reactant | Reaction pressure (Bar) | Reaction temperature (° C.) | Reactant flow rate (ml/min) | Hydrogen flow rate (L/hr) | Conversion (%) | Selectivity (%) | Yield (%) |
|---|---|---|---|---|---|---|---|
| DEHP | 40 | 80 | 0.054 | 7.03 | 98.68 | 99.86 | 98.54 |
| | 40 | 90 | 0.054 | 7.03 | 99.17 | 99.86 | 99.03 |

The results of the above embodiments 1 to 5 are summarized in a graph showing the effect of changes in magnesium content in a catalyst support on the yield in the FIGURE and Table 6. It can be seen that the yield can be improved after the addition of magnesium. Compared to the operating conditions at 40 bar and 80° C. (shown by a dashed line), the yield of di(2-ethylhexyl) phthalate (DEHP) hydrogenated products produced at 40 bar and 90° C. (shown by a solid line) is high than 99%, and there is an optimum ratio of magnesium content, so that the selectivity and the yield can be further increased up to 99.88% and 99.82%, respectively.

TABLE 6

| Operating conditions | 40 bar, 80° C. | | | 40 Bar, 90° C. | | |
|---|---|---|---|---|---|---|
| Mg weight percentages (%) | Conversion (%) | Selectivity (%) | Yield (%) | Conversion (%) | Selectivity (%) | Yield (%) |
| 0 | 95.80 | 85.61 | 82.87 | 99.23 | 95.9 | 95.16 |
| 2 | 98.64 | 99.82 | 98.46 | 99.79 | 99.72 | 99.51 |
| 4.5 | 99.83 | 99.87 | 99.70 | 99.95 | 99.88 | 99.82 |
| 6.1 | 99.81 | 99.85 | 99.66 | 99.93 | 99.86 | 99.79 |
| 8.5 | 98.68 | 99.86 | 98.54 | 99.17 | 99.86 | 99.03 |

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A process for making alicyclic polycarboxylic acids or their derivatives, corresponding alicyclic polycarboxylic acids or their derivatives being produced from aromatic polycarboxylic acids or their derivatives by hydrogenation reaction in a hydrogen atmosphere with a catalyst, the catalyst comprising (1) active metals of transition elements of group VIIIB of the periodic table of elements, and (2) a catalyst support comprising group IIA elements of the periodic table of elements and group IIIA elements of the periodic table of elements, wherein the group IIA elements of the periodic table of elements comprise one or combinations of more than two of magnesium (Mg), calcium (Ca), strontium (Sr), and barium (Ba), the group IIIA elements of the periodic table of elements comprise one or combinations of more than two of boron (B) and aluminum (Al), wherein the magnesium accounts for 4-6.5% by weight of the catalyst support, wherein the hydrogenation reaction pressure is 1-40 bar, wherein the hydrogenation reaction temperature is 50-100° C.

2. The process for making alicyclic polycarboxylic acids or their derivatives as claimed in claim 1, wherein the active metals of the transition elements of group VIIIB of the periodic table of elements are one or combinations of more than two of platinum (Pt), palladium (Pd), ruthenium (Ru), nickel (Ni), and rhodium (Rh).

3. The process for making alicyclic polycarboxylic acids or their derivatives as claimed in claim 1, the preferred active metal of the transition elements of group VIIIB of the periodic table of elements being ruthenium (Ru).

4. The process for making alicyclic polycarboxylic acids or their derivatives as claimed in claim 1, the preferred catalyst support of the group IIIA elements of the periodic table of elements being aluminum (Al).

5. The process for making alicyclic polycarboxylic acids or their derivatives as claimed in claim 1, wherein a shape or form of the catalyst support can be powder or a sphere, and a molding agent can be added to extrude a cylinder, a hollow ring cylinder, a three-petal shape, or a four-petal shape.

6. The process for making alicyclic polycarboxylic acids or their derivatives as claimed in claim 1, wherein the aromatic polycarboxylic acids are compounds formed with one or more than two of carboxylic acids, dicarboxylic acids, polycarboxylic acids, and hydroxycarboxylic acids contained in an aromatic structure, and benzene polycarboxylic acids include one or combinations of more than two of phthalic acid, isophthalic acid, terephthalic acid, trimellitic acid, trimesic acid, hemimellitic acid, and pyromellitic acid.

7. The process for making alicyclic polycarboxylic acids or their derivatives as claimed in claim 1, wherein the aromatic polycarboxylic acid derivatives are one or more than two of monoesters, diesters and polyesters of aromatic polycarboxylic acids, and benzene polycarboxylic esters include one or combinations of more than two of C1-C30 alkyl ester, C3-C30 cycloalkyl ester, and C1-C30 alkoxyalkyl ester.

8. The process for making alicyclic polycarboxylic acids or their derivatives as claimed in claim 1, wherein the aromatic polycarboxylic acid derivatives are esters including one or combinations of more than two of C2-C20 alkyl ester, C3-C20 cycloalkyl ester, and C2-C20 alkoxyalkyl ester.

9. The process for making alicyclic polycarboxylic acids or their derivatives as claimed in claim 1, wherein the aromatic polycarboxylic acid derivatives are esters including one or combinations of more than two of C3-C18 alkyl ester, C4-C18 cycloalkyl ester, and C3-C18 alkoxyalkyl ester.

10. The process for making alicyclic polycarboxylic acids or their derivatives as claimed in claim 1, wherein the aromatic polycarboxylic acids or their derivatives comprise one or combinations of more than two of dimethyl phthalate (DMP), dimethyl terephthalate (DMT), dimethyl isophthalate, diethyl phthalate (DEP), dibutyl phthalate (DBP), diisooctyl phthalate (DOP), diisononyl phthalate (DINP), benzyl butyl phthalate (BBP), diisodecyl phthalate (DIDP), and dioctyl terephthalate (DOTP).

11. The process for making alicyclic polycarboxylic acids or their derivatives as claimed in claim 1, wherein the aromatic polycarboxylic acids or their derivatives can be soluble in solvents or diluents.

12. The process for making alicyclic polycarboxylic acids or their derivatives as claimed in claim 1, wherein an operation mode of the hydrogenation reaction comprises one or combinations of more than two of batch type, semi-batch type, and continuous type.

13. The process for making alicyclic polycarboxylic acids or their derivatives as claimed in claim 1, wherein the hydrogenation reaction is carried out in a reactor comprising one or combinations of more than two of batchwise reactor, stir tank, trickle bed reactor, up-flow packed bed bubble column reactor, and multi-tube reactor.

* * * * *